(12) United States Patent
Buhr et al.

(10) Patent No.: US 7,326,718 B2
(45) Date of Patent: Feb. 5, 2008

(54) 8-SUBSTITUTED IMIDAZOPYRIDINES

(75) Inventors: Wilm Buhr, Constance (DE); Jörg Senn-Bilfinger, Constance (DE); Peter Jan Zimmermann, Radolfzell (DE)

(73) Assignee: Altana Pharma AG, Constance (DE)

( * ) Notice: Subject to any disclaimer, the term of this patent is extended or adjusted under 35 U.S.C. 154(b) by 60 days.

(21) Appl. No.: 10/534,741

(22) PCT Filed: Nov. 15, 2003

(86) PCT No.: PCT/EP03/12787

§ 371 (c)(1),
(2), (4) Date: May 12, 2005

(87) PCT Pub. No.: WO2004/046144

PCT Pub. Date: Jun. 3, 2004

(65) Prior Publication Data

US 2006/0100234 A1 May 11, 2006

(30) Foreign Application Priority Data

Nov. 19, 2002 (EP) ................... 02025866

(51) Int. Cl.
*C07D 471/02* (2006.01)
*C07D 491/02* (2006.01)
*C07D 498/02* (2006.01)
*A01N 43/42* (2006.01)
*A61K 31/44* (2006.01)

(52) U.S. Cl. ...................... 514/300; 546/121
(58) Field of Classification Search ............... 546/121; 514/300
See application file for complete search history.

(56) References Cited

U.S. PATENT DOCUMENTS

| 5,112,834 A | 5/1992 | Senn-Bilfinger |
| 6,197,783 B1 | 3/2001 | Senn-Bilfinger et al. |

FOREIGN PATENT DOCUMENTS

| EP | 0 368 158 A1 | 5/1990 |
| WO | 88/08843 A2 | 11/1988 |
| WO | 89/00570 A1 | 1/1989 |
| WO | 90/05136 A | 5/1990 |
| WO | 9005136 * | 5/1990 |
| WO | 98/42707 A1 | 10/1998 |
| WO | 98/54188 A1 | 12/1998 |
| WO | 99/55705 A1 | 11/1999 |
| WO | 99/55706 A1 | 11/1999 |
| WO | 00/17200 A1 | 3/2000 |
| WO | 00/26217 A1 | 5/2000 |
| WO | 00/63211 A1 | 10/2000 |
| WO | 01/72754 A1 | 10/2001 |
| WO | 01/72755 A1 | 10/2001 |
| WO | 01/72756 A1 | 10/2001 |
| WO | 01/72757 A1 | 10/2001 |
| WO | 02/060440 A1 | 8/2002 |
| WO | 02/060441 A1 | 8/2002 |
| WO | 02/060442 A1 | 8/2002 |

OTHER PUBLICATIONS

Messaouik D., International Journal of Pharmaceutics, "comparative study and optimisation of the administration mode of three proton pump inhibitors by nasogastric tube", vol. 299, pp. 65-72.*
Chang-Young Lim, Journal of Clinical Microbiology, "Detection of *Helicobacter pylori* in Gastric Mucosa of patients with gastroduodenal diseases by PCR-Restriction analysis using the RNA polymerase gene", vol. 41, pp. 3387-3391.*
Kaminski, J.J., et al., "Antiulcer Agents. 1. Gastric Antisecretory and Cytoprotective Properties of Substituted Imidazo[1,2-a]pyridines", *J. Med. Chem.*, vol. 28, pp. 876-892, (1985).
Kaminski, J.J., et al., "Antiulcer Agents. 6. Analysis of the in Vitro Biochemical and in Vivo Gastric Antisecretory Activity of Substituted Imidazo[1,2-a]pyridines and Related Analogues Using Comparative Molecular Field Analysis and Hypothetical Active Site Lattice Methodologies", *J. Med. Chem.*, vol. 40, pp. 427-436, (1997).
Wurst, W., et al., "Current Status of Acid Pump Antagonists (Reversible PPIs)", *Yale Journal of Biology and Medicine*, vol. 69, pp. 233-242, (1996).

* cited by examiner

*Primary Examiner*—Margaret D. Seamani
*Assistant Examiner*—Niloofar Rahmani
(74) *Attorney, Agent, or Firm*—The Nath Law Group; Joshua B. Goldberg; Sheldon M. McGee

(57) ABSTRACT

The present invention relates to 8-substituted imidazopyridines of a certain formula (1)

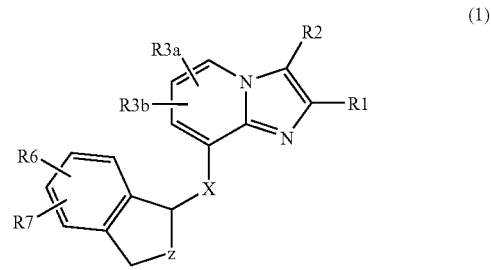

in which the substitutents and symbols have the meanings indicated in the description. The compounds have gastric secretion inhibiting and excellent gastric and intestinal protective action properties.

12 Claims, No Drawings

1

8-SUBSTITUTED IMIDAZOPYRIDINES

TECHNICAL FIELD

The invention relates to novel compounds, which are used in the pharmaceutical industry as active compounds for the production of medicaments.

PRIOR ART

In international patent applications WO98/42707 (=U.S. Pat. No. 6,197,783), WO98/54188, WO00/17200, WO00/26217, WO00/63211, WO01/72756, WO01/72754, WO01/72755 and WO01/72757, tricyclic imidazopyridine derivatives having a very specific substitution pattern are disclosed, which are said to be suitable for the treatment of gastric and intestinal diseases. In international patent applications WO88/08843, WO89/00570 (=U.S. Pat. No. 5,112,834) and WO90/05136 imidazopyridine derivatives are disclosed, which are likewise said to be suitable for the treatment of gastric and intestinal diseases

SUMMARY OF THE INVENTION

The invention relates to compounds of the formula 1

(1)

in which
R1 is hydrogen, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl or hydroxy-1-4C-alkyl,
R2 is hydrogen, 1-4C-alkyl, aryl, 3-7C-cycloalkyl, 3-7C-cycloalkyl-1-4C-alkyl, 1-4C-alkoxycarbonyl, hydroxy-1-4C-alkyl, halogen, 2-4C-alkenyl, 2-4C-alkynyl, fluoro-1-4C-alkyl, 1-4C-alkyl-aminomethyl or cyanomethyl,
R3a is hydrogen, halogen, fluoro-1-4C-alkyl, 1-4C-alkyl, 2-4C-alkenyl, 2-4C-alkynyl, carboxyl, —CO-1-4C-alkoxy, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the group —CO—NR31R32,
R3b is hydrogen, halogen, fluoro-1-4C-alkyl, 1-4C-alkyl, 2-4C-alkenyl, 2-4C-alkynyl, carboxyl, —CO-1-4C-alkoxy, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the group —CO—NR31R32,
where
R31 is hydrogen, hydroxyl, 1-7C-alkyl, hydroxy-1-4C-alkyl or 1-4C-alkoxy-1-4C-alkyl and
R32 is hydrogen, 1-7C-alkyl, hydroxy-1-4C-alkyl or 1-4C-alkoxy-1-4C-alkyl,
or where
R31 and R32 together, including the nitrogen atom to which both are bonded, are a pyrrolidino, piperidino, piperazino, N-1-4C-alkylpiperazino or morpholino group, Z has the meaning —CHR4- or —CHR4-CHR5-
where
R4 is hydrogen, 1-7C-alkyl, 2-7C-alkenyl, hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino,
R5 is hydrogen, 1-7C-alkyl, 2-7C-alkenyl, hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino,
R6 is hydrogen, 1-4C-alkyl, hydroxy-1-4C-alkyl, 1-4C-alkoxy, 1-4C-alkoxy-1-4C-alkyl, 2-4C-alkenyloxy, 1-4C-alkylcarbonyl, carboxyl, 1-4C-alkoxycarbonyl, carboxy-1-4C-alkyl, 1-4C-alkoxycarbonyl-1-4C-alkyl, halogen, hydroxyl, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl,
R7 is hydrogen, 1-4C-alkyl, 1-4C-alkoxy, 1-4C-alkoxycarbonyl, halogen, trifluoromethyl or hydroxyl,
X is O (oxygen) or NH, and
aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy, hydroxyl and cyano, and their salts, with the provisos that
(1) R3a is not hydrogen, halogen, 1-4C-alkoxy or —CO-1-4C-alkoxy when R3b is hydrogen, Z has the meaning —CHR4- and R4 is hydrogen or 1-7C-alkyl,
(2) R3a is not hydrogen, halogen, 1-4C-alkoxy or —CO-1-4C-alkoxy when R3b is hydrogen, Z has the meaning —CHR4-CHR5-, R4 is hydrogen or 1-7C-alkyl and R5 is hydrogen or 1-7C-alkyl,
(3) R3a is not hydrogen or halogen when R3b is hydrogen, Z has the meaning —CHR4- and R4 is hydroxyl,
(4) R3a is not hydrogen or halogen when R3b is hydrogen, Z has the meaning —CHR4-CHR5-, one of R4 and R5 is hydroxyl and the other is hydrogen or 1-7C-alkyl,
(5) R3a is not hydrogen when R3b is hydrogen, X is O (oxygen), Z has the meaning —CHR4- and R4 is 1-4C-alkoxy, 3-7C-cycloalkoxy, 1-4C-alkoxy-1-4C-alkoxy or 1-4C-alkylcarbonyloxy and
(6) R3a is not hydrogen when R3b is hydrogen, X is O (oxygen), Z has the meaning —CHR4-CHR5-, one of R4 and R5 1-4C-alkoxy, 3-7C-cycloalkoxy, 1-4C-alkoxy-4C-alkoxy or 1-4C-alkylcarbonyloxy and the other is hydrogen.

1-4C-Alkyl represents straight-chain or branched alkyl groups having 1 to 4 carbon atoms. Examples which may be mentioned are the butyl, isobutyl, sec-butyl, tert-butyl, propyl, isopropyl, ethyl and the methyl group.

3-7C-Cycloalkyl represents cyclopropyl, cyclobutyl, cyclopentyl, cyclohexyl and cycloheptyl, of which cyclopropyl, cyclobutyl and cyclopentyl are preferred.

3-7C-Cycloalkyl-1-4C-alkyl represents one of the aforementioned 1-4C-alkyl groups, which is substituted by one of the aforementioned 3-7C-cycloalkyl groups. Examples which may be mentioned are the cyclopropylmethyl, the cyclohexylmethyl and the cyclohexylethyl group.

1-4C-Alkoxy represents groups, which in addition to the oxygen atom contain a straight-chain or branched alkyl group having 1 to 4 carbon atoms. Examples which may be mentioned are the butoxy, isobutoxy, sec-butoxy, tert-butoxy, propoxy, isopropoxy and preferably the ethoxy and methoxy group.

1-4C-Alkoxy-1-4C-alkyl represents one of the aforementioned 1-4C-alkyl groups, which is substituted by one of the aforementioned 1-4C-alkoxy groups. Examples which may be mentioned are the methoxymethyl, the methoxyethyl group and the butoxyethyl group.

1-4C-Alkoxycarbonyl (—CO-1-4C-alkoxy) represents a carbonyl group, to which one of the aforementioned 1-4C-alkoxy groups is bonded. Examples which may be mentioned are the methoxycarbonyl ($CH_3O-C(O)-$) and the ethoxycarbonyl group ($CH_3CH_2O-C(O)-$).

2-4C-Alkenyl represents straight-chain or branched alkenyl groups having 2 to 4 carbon atoms. Examples which may be mentioned are the 2-butenyl, 3-butenyl, 1-propenyl and the 2-propenyl group (allyl group).

2-4C-Alkynyl represents straight-chain or branched alkynyl groups having 2 to 4 carbon atoms. Examples which may be mentioned are the 2-butynyl, 3-butynyl, and preferably the 2-propynyl, group (propargyl group).

Fluoro-1-4C-alkyl represents one of the aforementioned 1-4C-alkyl groups, which is substituted by one or more fluorine atoms. An example which may be mentioned is the trifluoromethyl group.

Hydroxy-1-4C-alkyl represents aforementioned 1-4C-alkyl groups, which are substituted by a hydroxy group. Examples which may be mentioned are the hydroxymethyl, the 2-hydroxyethyl and the 3-hydroxypropyl group.

Halogen within the meaning of the invention is bromo, chloro and fluoro.

1-4-Alkoxy-1-4C-alkoxy represents one of the aforementioned 1-4C-alkoxy groups, which is substituted by a further 1-4C-alkoxy group. Examples which may be mentioned are the groups 2-(methoxy)ethoxy ($CH_3-O-CH_2-CH_2-O-$) and 2-(ethoxy)ethoxy ($CH_3-CH_2-O-CH_2-CH_2-O-$).

1-4C-Alkoxy-1-4C-alkoxy-1-4C-alkyl represents one of the aforementioned 1-4C-alkoxy-1-4C-alkyl groups, which is substituted by one of the aforementioned 1-4C-alkoxy groups. An example which may be mentioned is the group 2-(methoxy)ethoxymethyl ($CH_3-O-CH_2-CH_2-O-CH_2-$).

Fluoro-1-4C-alkoxy-1-4C-alkyl represents one of the aforementioned 1-4C-alkyl groups, which is substituted by a fluoro-1-4C-alkoxy group. Fluoro-1-4C-alkoxy in this case represents one of the aforementioned 1-4C-alkoxy groups, which is completely or mainly substituted by fluorine. Examples of completely or mainly fluoro-substituted 1-4C-alkoxy groups which may be mentioned are the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy group.

1-7C-Alkyl represents straight-chain or branched alkyl groups having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and the methyl group.

2-7C-Alkenyl represents straight-chain or branched alkenyl groups having 2 to 7 carbon atoms. Examples which may be mentioned are the 2-butenyl, 3-butenyl, 1-propenyl, the 2-propenyl (allyl) and the vinyl group. The aforementioned 2-4C-alkenyl groups are preferred.

Oxo-substituted 1-4C-alkoxy represents a 1-4C-alkoxy group, which instead of a methylene group contains a carbonyl group. An example which may be mentioned is the 2-oxopropoxy group.

3-7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkyl-1-4C-alkoxy represents one of the aforementioned 1-4C-alkoxy groups, which is substituted by one of the aforementioned 3-7C-cycloalkyl groups. Examples which may be mentioned are the cyclopropylmethoxy, the cyclobutylmethoxy and the cyclohexylethoxy group.

Hydroxy-1-4C-alkoxy represents aforementioned 1-4C-alkoxy groups, which are substituted by a hydroxy group. A preferred example which may be mentioned is the 2-hydroxyethoxy group.

1-4C-Alkoxy-1-4C-alkoxy-1-4C-alkoxy represents one of the aforementioned 1-4C-alkoxy groups, which is substituted by one of the aforementioned 1-4C-alkoxy-1-4C-alkoxy groups. A preferred example which may be mentioned is the methoxyethoxyethoxy group.

3-7C-Cycloalkoxy-1-4C-alkoxy represents one of the aforementioned 1-4C-alkoxy groups, which is substituted by one of the aforementioned 3-7C-cycloalkoxy groups. Examples which may be mentioned are the cyclopropoxymethoxy, the cyclobutoxymethoxy and the cyclohexyloxyethoxy group.

3-7C-Cycloalkyl-1-4C-alkoxy-1-4C-alkoxy represents one of the aforementioned 1-4C-alkoxy groups, which is substituted by one of the aforementioned 3-7C-cycloalkyl-1-4C-alkoxy groups. Examples which may be mentioned are the cyclopropylmethoxyethoxy, the cyclobutylmethoxyethoxy and the cyclohexylethoxyethoxy group.

1-4C-Alkylcarbonyl represents a group, which in addition to the carbonyl group contains one of the aforementioned 1-4C-alkyl groups. An example which may be mentioned is the acetyl group.

1-4C-Alkylcarbonyloxy represents a 1-4C-alkylcarbonyl group which is bonded to an oxygen atom. An example which may be mentioned is the acetoxy group ($CH_3CO-O-$).

Halo-1-4C-alkoxy represents 1-4C-alkoxy groups which are completely or mainly substituted by halogen. "Mainly" in this connection means that more than half of the hydrogen atoms in the 1-4C-alkoxy groups are replaced by halogen atoms. Halo-1-4C-alkoxy groups are primarily chloro- and/or in particular fluoro-substituted 1-4C-alkoxy groups.

Examples of halogen-substituted 1-4C-alkoxy groups which may be mentioned are the 2,2,2-trichloroethoxy, the hexachloroisopropoxy, the pentachloroisopropoxy, the 1,1,1-trichloro-3,3,3-trifluoro-2-propoxy, the 1,1,1-trichloro-2-methyl-2-propoxy, the 1,1,1-trichloro-2-propoxy, the 3-bromo-1,1,1-trifluoro-2-propoxy, the 3-bromo-1,1,1-trifluoro-2-butoxy, the 4-bromo-3,3,4,4-tetrafluoro-1-butoxy, the chlorodifluoromethoxy, the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy group.

Mono- or di-1-4C-alkylamino represents an amino group, which is substituted by one or by two—identical or different—groups from the aforementioned 1-4C-alkyl groups. Examples which may be mentioned are the dimethylamino, the diethylamino and the diisopropylamino group.

1-4C-Alkylcarbonyl represents a group, which in addition to the carbonyl group contains one of the aforementioned 1-4C-alkyl groups. An example which may be mentioned is the acetyl group.

1-4C-Alkylcarbonylamino represents an amino group to which a 1-4C-alkylcarbonyl group is bonded. Examples which may be mentioned are the propionylamino ($C_3H_7C(O)NH-$) and the acetylamino group (acetamido group) ($CH_3C(O)NH-$).

1-4C-Alkoxycarbonylamino represents an amino group, which is substituted by one of the aforementioned 1-4C-alkoxycarbonyl groups. Examples, which may be mentioned, are the ethoxycarbonylamino and the methoxycarbonylamino group.

Mono- or di-1-4C-alkylamino-1-4C-alkylcarbonyloxy represents a 1-4C-alkylcarbonyloxy group, which is substituted by one of the aforementioned mono- or di-1-4C-alkylamino groups. Examples, which may be mentioned, are the dimethylamino-methylcarbonyloxy and the dimethylamino-ethylcarbonyloxy group.

1-4C-Alkoxy-1-4C-alkoxycarbonyl represents a carbonyl group, to which one of the aforementioned 1-4C-alkoxy-1-4C-alkoxy groups is bonded. Examples which may be mentioned are the 2-(methoxy)-ethoxycarbonyl ($CH_3-O-CH_2CH_2-O-CO-$) and the 2-(ethoxy)ethoxycarbonyl group ($CH_3CH_2-O-CH_2CH_2-O-CO-$).

1-4C-Alkoxy-1-4C-alkoxycarbonylamino represents an amino group, which is substituted by one of the aforementioned 1-4C-alkoxy-1-4C-alkoxycarbonyl groups. Examples which may be mentioned are the 2-(methoxy)ethoxycarbonylamino and the 2-(ethoxy)ethoxycarbonylamino group.

2-4C-Alkenyloxy represents groups, which in addition to the oxygen atom contain one of the above-mentioned 2-4C-alkenyl groups. Examples, which may be mentioned, are the 2-butenyloxy, 3-butenyloxy, 1-propenyloxy and the 2-propenyloxy group (allyloxy group).

Carboxy-1-4C-alkyl represents 1-4C-alkyl groups which are substituted by a carboxyl group. Examples, which may be mentioned, are the carboxymethyl and the 2-carboxyethyl group.

1-4C-Alkoxycarbonyl-1-4C-alkyl represents 1-4C-alkyl groups, which are substituted by one of the abovementioned 1-4C-alkoxycarbonyl groups. Examples, which may be mentioned, are the methoxycarbonylmethyl and the ethoxycarbonylmethyl group.

Possible salts of compounds of the formula I—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are used in salt preparation—depending on whether a mono- or polybasic acid is concerned and on which salt is desired—in an equimolar quantitative ratio or one differing there from.

Pharmacologically intolerable salts, which can initially be obtained, for example, as process products in the production of the compounds according to the invention on the industrial scale, are converted into the pharmacologically tolerable salts by processes known to the person skilled in the art.

It is known to the person skilled in the art that the compounds according to invention and their salts, if, for example, they are isolated in crystalline form, can contain various amounts of solvents. The invention therefore also comprises all solvates and in particular all hydrates of the compounds of the formula I, and also all solvates and in particular all hydrates of the salts of the compounds of the formula I.

The compounds of the formula I have up to three chiral centres in the parent structure. The invention thus relates to all conceivable stereoisomers in any desired mixing ratio to one another, including the pure enantiomers, which are a preferred subject of the invention.

One embodiment (embodiment 1) of the invention are compounds of the formula 1, in which Z has the meaning —CHR4- and their salts.

The compounds of embodiment 1 are characterized by the following formula 1-1

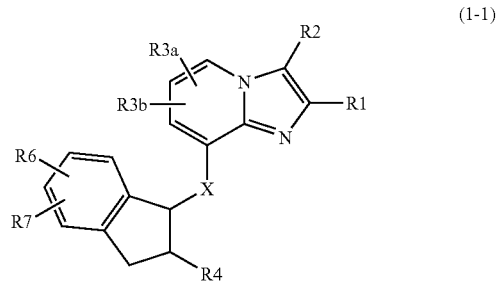

(1-1)

in which R1, R2, R3a, R3b, R4, R6, R7 and X have the abovementioned meanings.

Another embodiment (embodiment 2) of the invention are compounds of the formula 1, in which Z has the meaning —CHR4-CHR5- and their salts.

The compounds of embodiment 2 are characterized by the following formula 1-2

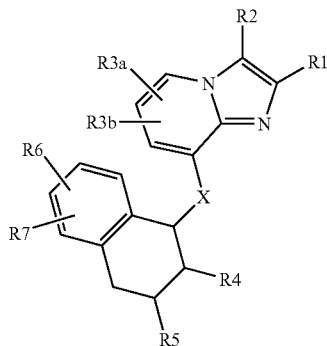

(1-2)

in which R1, R2, R3a, R3b, R4, R5, R6, R7 and X have the abovementioned meanings.

Compounds to be emphasized are those of the formula 1, in which

R1 is hydrogen, 1-4C-alkyl, 3-7C-cycloalkyl, 1-4C-alkoxy-1-4C-alkyl, 2-4C-alkynyl or fluoro-1-4C-alkyl, R2 is hydrogen, 1-4C-alkyl, hydroxy-1-4C-alkyl, halogen, 2-4C-alkenyl, 2-4C-alkynyl or fluoro-1-4C-alkyl, R3a is in the 6-position and denotes fluoro-1-4C-alkyl, 1-4C-alkyl, 2-4C-alkenyl, 2-4C-alkynyl, carboxyl, —CO-1-4C-alkoxy, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the group —CO—NR31R32, where R31 is hydrogen, hydroxyl, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino, piperazino, N-1-4C-alkylpiperazino or morpholino group, R3b is hydrogen, Z has the meaning —CHR4- or —CHR4-CHR5- where

R4 is hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino, R5 is hydrogen, 1-7C-alkyl, 2-7C-alkenyl, hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino, R6 is hydrogen, 1-4C-alkyl, hydroxy-1-4C-alkyl, 1-4C-alkoxy, 1-4C-alkoxy-1-4C-alkyl, 2-4C-alkenyloxy, 1-4C-alkylcarbonyl, carboxyl, 1-4C-alkoxycarbonyl, carboxy-1-4C-alkyl, 1-4C-alkoxycarbonyl-1-4C-alkyl, halogen, hydroxyl, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R7 is hydrogen, 1-4C-alkyl, 1-4C-alkoxy, 1-4C-alkoxycarbonyl, halogen, trifluoromethyl or hydroxyl, X is O (oxygen) or NH, and their salts.

Compounds to be particularly emphasized are those of the formula 1, in which

R1 is 1-4C-alkyl,

R2 is hydrogen, 1-4C-alkyl or halogen,

R3a is in the 6-position and denotes carboxyl, —CO-1-4C-alkoxy, hydroxy-1-4C-alkyl, 1-4C-alkoxy-1-4C-alkyl or the group —CO—NR31R32, where R31 is hydrogen, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino, piperazino, N-1-4C-alkylpiperazino or morpholino group, R3b is hydrogen, Z has the meaning —CHR4- or —CHR4-CHR5- where

R4 is hydroxyl,

R5 is hydrogen,

R6 is hydrogen, 1-4C-alkyl or 1-4C-alkoxy,

R7 is hydrogen,

X is O (oxygen) or NH, and their salts.

Compounds of embodiment 1 to be particularly emphasized are those of the formula 1-1, in which R1 is 1-4C-alkyl, R2 is hydrogen, 1-4C-alkyl or halogen, R3a is in the 6-position and denotes carboxyl, —CO-1-4C-alkoxy, hydroxy-1-4C-alkyl, 1-4C-alkoxy-1-4C-alkyl or the group —CO—NR31R32, where R31 is hydrogen, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino, piperazino, N-1-4C-alkylpiperazino or morpholino group, R3b is hydrogen, R4 is hydroxyl, R6 is hydrogen, 1-4C-alkyl or 1-4C-alkoxy, R7 is hydrogen, X is O (oxygen) or NH, and their salts.

Among the compounds of embodiment 1, the optically pure compounds of the formula 1-1*

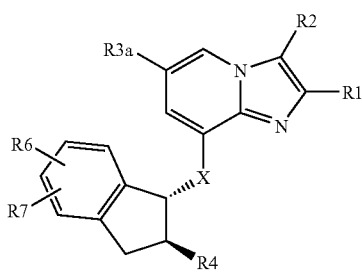

(1-1*)

are preferred.

Among the compounds of embodiment 2, the optically pure compounds of the formula 1-2*

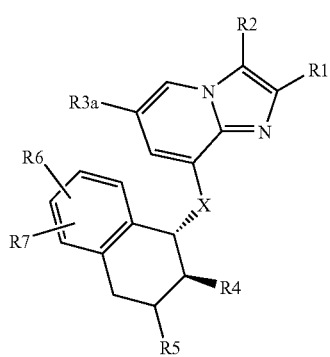

(1-2*)

are preferred.

Preferred exemplary compounds of the formula 1-2* are those, in which
R1 is 1-4C-alkyl,
R2 is 1-4C-alkyl,
R3a is in the 6-position and denotes carboxyl, —CO-1-4C-alkoxy, 1-4C-alkoxy-1-4C-alkyl or the group —CO—NR31R32,
  where
    R31 is hydrogen, 1-4C-alkyl, hydroxy-1-4C-alkyl or 1-4C-alkoxy-1-4C-alkyl and
    R32 is hydrogen or 1-4C-alkyl,
R4 is hydroxyl,
R5 is hydrogen,
R6 is hydrogen,
R7 is hydrogen,
X is O (oxygen) or NH, and their salts.

Selected particularly preferred compounds of the formula 1-2* are those, in which
R1 is 1-4C-alkyl,
R2 is 1-4C-alkyl,
R3a is in the 6-position and denotes the group —CO—NR31R32,
  where
    R31 is hydrogen, 1-4C-alkyl or 1-4C-alkoxy-1-4C-alkyl and
    R32 is hydrogen or 1-4C-alkyl,
R4 is hydroxyl,
R5 is hydrogen,
R6 is hydrogen,
R7 is hydrogen,
X is O (oxygen), and their salts.

Preferred compounds are those of embodiment 1.

Preferred exemplary compounds of the formula 1-1* are accordingly those, in which
R1 is 1-4C-alkyl,
R2 is hydrogen, 1-4C-alkyl or halogen,
R3a is in the 6-position and denotes carboxyl, —CO-1-4C-alkoxy, 1-4C-alkoxy-1-4C-alkyl, 1-4C-alkoxy-1-4C-alkoxy-1-4C-alkyl or the group —CO—NR31R32,
  where
    R31 is hydrogen, 1-7C-alkyl, hydroxy-1-4C-alkyl or 1-4C-alkoxy-1-4C-alkyl and
    R32 is hydrogen, 1-7C-alkyl, hydroxy-1-4C-alkyl or 1-4C-alkoxy-1-4C-alkyl,
  or where
    R31 and R32 together, including the nitrogen atom to which both are bonded, are a pyrrolidino, piperidino, piperazino, N-1-4C-alkylpiperazino or morpholino group,
R4 is hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino,
R6 is hydrogen, 1-4C-alkyl, 1-4C-alkoxy or halogen,
R7 is hydrogen,
X is O (oxygen) or NH, and their salts.

Particularly preferred compounds of the formula 1-1* are those, in which
R1 is 1-4C-alkyl,
R2 is 1-4C-alkyl,
R3a is in the 6-position and denotes carboxyl, —CO-1-4C-alkoxy, 1-4C-alkoxy-1-4C-alkyl or the group —CO—NR31R32,
  where
    R31 is hydrogen, 1-4C-alkyl, hydroxy-1-4C-alkyl or 1-4C-alkoxy-1-4C-alkyl and
    R32 is hydrogen or 1-4C-alkyl,
R4 is hydroxyl,
R6 is hydrogen,
R7 is hydrogen,
X is O (oxygen) or NH, and their salts.

Selected particularly preferred compounds of the formula 1-1* are those, in which
R1 is 1-4C-alkyl,
R2 is 1-4C-alkyl,
R3a is in the 6-position and denotes the group —CO—NR31R32,
  where
    R31 is hydrogen, 1-4C-alkyl or 1-4C-alkoxy-1-4C-alkyl and
    R32 is hydrogen or 1-4C-alkyl,
R4 is hydroxyl,
R6 is hydrogen, 1-4C-alkyl or 1-4C-alkoxy,
R7 is hydrogen,
X is O (oxygen) or NH, and their salts.

Within the selected particularly preferred compounds of the formula 1-1*, those in which X is O (oxygen) have to be singled out.

Particularly preferred exemplary compounds are those of formula 1-1* in which R1 is methyl, R6 is hydrogen, R7 is hydrogen and the substituents and groups R2, R3a (in 6-position), R4 and X have the meanings given in the following table 1,

TABLE 1

| R2 | R3a | R4 | X |
|---|---|---|---|
| CH₃ | CON(CH₃)₂ | OH | NH |
| H | CON(CH₃)₂ | OH | NH |
| Cl | CON(CH₃)₂ | OH | NH |
| CH₃ | CONH₂ | OH | NH |
| H | CONH₂ | OH | NH |
| Cl | CONH₂ | OH | NH |
| CH₃ | CON(CH₃)₂ | OH | O |
| H | CON(CH₃)₂ | OH | O |
| Cl | CON(CH₃)₂ | OH | O |
| CH₃ | CONH₂ | OH | O |
| H | CONH₂ | OH | O |
| Cl | CONH₂ | OH | O |
| CH₃ | CONHCH₂CH₂OH | OH | NH |
| H | CONHCH₂CH₂OH | OH | NH |
| Cl | CONHCH₂CH₂OH | OH | NH |
| CH₃ | CH₂OCH₃ | OH | NH |
| H | CH₂OCH₃ | OH | NH |
| Cl | CH₂OCH₃ | OH | NH |
| CH₃ | CONHCH₂CH₂OH | OH | O |
| H | CONHCH₂CH₂OH | OH | O |
| Cl | CONHCH₂CH₂OH | OH | O |
| CH₃ | CH₂OCH₃ | OH | O |
| H | CH₂OCH₃ | OH | O |
| Cl | CH₂OCH₃ | OH | O | and the salts of these compounds.

Particularly preferred are the compounds given as final products in the examples, and the salts of these compounds.

The compounds according to the invention can be synthesised from corresponding starting compounds, for example according to the reaction schemes given below. The synthesis is carried out in a manner known to the expert, for example as described in more detail in the following examples.

The starting compounds are known, for example from WO99/55706 (e.g. methyl 8-amino-2,3-dimethylimidazo[1,2-a]pyridine-6-carboxylate), WO01/72754 (e.g. ethyl 8-benzyloxy-2,3-dimethyl-imidazo[1,2-a]pyridine-6-carboxylate) or WO01/72757 (e.g. 8-benzyloxy-6-methoxymethyl-2,3-dimethylimidazo[1,2-a]pyridine) or they can be prepared using analogous process steps. 1,2-Epoxyindane is described for example in W. F. Whitmore; A. I. Gebhart, *J. Am. Chem. Soc.* 1942, 64, 912; for enantiomeric pure 1,2-epoxyindane see e.g. D. R. Boyd; N. D. Sharma; A. E. Smith, *J. Chem. Soc. Perkin Trans.* I 1982, 2767. In general, substituted alkyl-, alkoxy- or halogeno-epoxyindanes can be prepared from the corresponding substituted indenes by methods known from literature (e.g. epoxidation) or by the general method known to the expert as depicted in scheme 1.

Scheme 1:
Preparation of substituted epoxyindanes

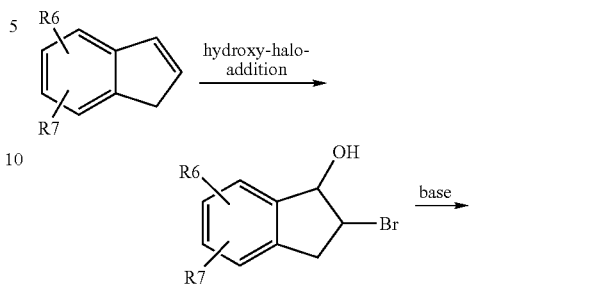

Scheme 2:
Preparation of compounds 1 where X = O (oxygen) or NH, Z = ——CHR4——, R4 = hydroxyl and any desired substituents R1, R2, R3a, R3b, R6 and R7

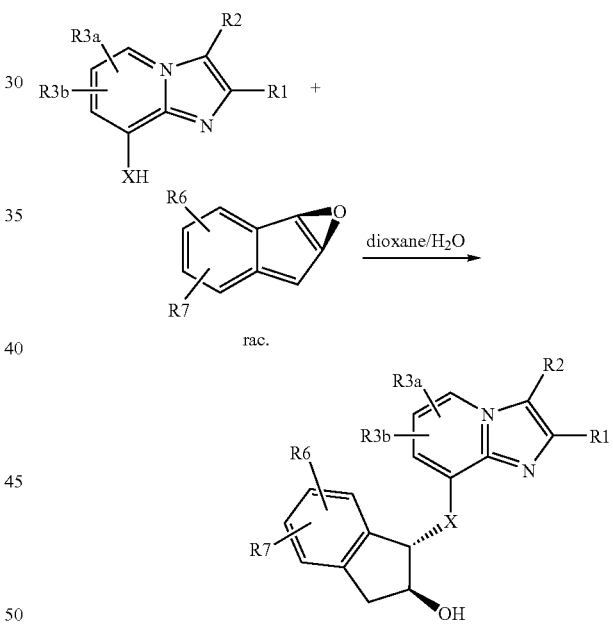

The reaction steps outlined above are carried out in a manner known per se, e.g. as described in more detail in the examples. The derivatization, if any, of the compounds obtained according to the above Scheme 2 (e.g. conversion of a group R3a into another group R3a, or conversion of the hydroxyl group into an alkoxy or ester group) is likewise carried out in a manner known per se, e.g. as described by way of example in international patent applications WO 00/17200 and WO01/72757. If compounds where R3a=—CO—NR31R32 are desired, an appropriate derivatization can be performed in a manner known per se (conversion of an ester into an amide) at the stage of the 8-benzyloxy-6-ethoxycarbonyl compound (cf. WO 01/72757) or after the debenzylation/reduction, or alternatively also at a later point in time. The debenzylation/reduction itself is likewise carried out in a manner known per se, for example using hydrogen/Pd(0).

Starting compounds having various substituents R1 and R2 are known, or they can be prepared in a known manner in analogy to known compounds. Alternatively, derivatizations—for example at position 3—can also be carried out at the stage of the compounds 1. It is thus possible, for example, starting from compounds where R2=H, to prepare compounds where R2=CH$_2$OH (by Vilsmeier reaction and subsequent reduction), where R2=Cl or Br (by chlorination or bromination), where R2=propynyl (from the corresponding bromo compound using the Sonogashira reaction) or where R2=alkoxycarbonyl (from the corresponding bromo compound by metal catalysed carbonylation).

The following examples serve to illustrate the invention in greater detail without restricting it. Likewise, further compounds of the formula 1 whose preparation is not described explicitly can be prepared in an analogous manner or in a manner familiar per se to the person skilled in the art using customary process techniques. The abbreviation min stands for minute(s), h for hour(s).

EXAMPLES

1. Methyl 8-(trans-2,3-dihydro-2-hydroxy-1-indenylamino)-2,3-dimethyl-imidazo[1,2-a]pyridine-6-carboxylate 10.0 g (45.7 mmol) methyl 8-amino-2,3-dimethylimidazo[1,2-a]pyridine-6-carboxylate and 18.1 g (137 mmol) 1,2-epoxyindane are suspended in 300 ml dioxane and 100 ml water. The reaction mixture is stirred at 100° C. for 2.5 d. After cooling down in an ice bath, the precipitate is collected and washed with water. The product is suspended in a mixture of 2-propanol and acetone (1:1) and filtered by suction. After drying in vacuo at 50° C., 12.4 g (77%) of the title compound are isolated as a colourless solid (m.p. 261-262° C.).

2. 8-(trans-2,3-Dihydro-2-hydroxy-1-indenylamino)-2,3-dimethyl-imidazo[1,2-a]pyridine-6-carboxylic acid 2.0 g (5.7 mmol) methyl 8-(trans-2,3-dihydro-2-hydroxy-1-indenylamino)-2,3-dimethyl-imidazo[1,2-a]pyridine-6-carboxylate are suspended in 100 ml dioxane and 20 ml 2N aqueous sodium hydroxide and heated to reflux. After 1 h the reaction mixture is cooled down, evaporated in vacuo to ¼ of its volume and 50 ml water are added. The pH of the mixture is adjusted to pH=7 by adding 2N hydrochloric acid and the flask is placed in an ice bath. After 30 min, the precipitate is collected, washed with water and dried in vacuo at 50° C. to yield 1.4 g (73%) of the title compound (m.p. 246-249° C.).

3. 8-(trans-2,3-Dihydro-2-hydroxy-1-indenylamino)-6-[N-(2-methoxyethyl)-amino-carbony]-2,3-dimethyl-imidazol-[1,2-a]pyridine 1.4 g (4.1 mmol) 8-(trans-2,3-dihydro-2-hydroxy-1-indenylamino)-2,3-dimethyl-imidazo[1,2-a]pyridine-6-carboxylic acid and 1.7 g (5.3 mmol) O-(1H-benzotriazol-1-yl)-N,N,N',N'-tetramethyluronium tetrafluoroborate (TBTU) are suspended in 100 ml dichloromethane. After stirring for 20 min, 0.71 ml (8.2 mmol) 2-methoxyethylamine are added to the reaction mixture. After 1 h at room temperature, a further amount of 0.2 ml (2.3 mmol) 2-methoxyethylamine is added and stirring is continued for 1 h. The reaction mixture is extracted with saturated aqueous sodium hydrogencarbonate, the organic phase is separated, dried over anhydrous magnesium sulphate and evaporated. Purification of the residue by column chromatography on silica gel using dichloromethane:methanol (20:1) and crystallization from methanol/diethyl ether yields 0.9 g (56%) of the title compound as a colourless solid (m.p. 190-191° C.).

4. 8-(trans-2,3-Dihydro-2-hydroxy-1-indenylamino)-6-(N,N-dimethylamino-carbonyl)-2,3-dimethyl-imidazo[1,2-a]pyridine 3.0 g (8.9 mmol)-8-(trans-2,3-dihydro-2-hydroxy-1-indenylamino)-2,3-dimethyl-imidazo[1,2-a]pyridine-6-carboxylic acid and 3.7 g (11.6 mmol) —O-(1H-benzotriazol-1-yl)-N,N,N',N'-tetramethyluronium tetrafluoroborate (TBTU) are suspended in 150 ml dichloromethane and 3.2 ml (17.8 mmol) dimethylamine (5.6 M in ethanol) are added to the reaction mixture. After stirring for 16 h at room temperature, the reaction mixture is extracted with saturated aqueous sodium hydrogencarbonate. The organic phase is separated, dried over anhydrous magnesium sulphate and evaporated. The residue is dissolved in 10 ml dichloromethane and 50 ml diethyl ether are added. After stirring for 30 min, the precipitate is collected, washed with diethyl ether and dried in vacuo to give 2.35 g (73%) of the title compound as a colourless solid (m.p. 148-149° C.).

5. 8-(trans-2,3-Dihydro-2-hydroxy-1-indenylamino)-6-(N-methylamino-carbonyl)-2,3-dimethyl-imidazo[1,2-a]pyridine 1.0 g (3.0 mmol) 8-(trans-2,3-dihydro-2-hydroxy-1-indenylamino)-2,3-dimethyl-imidazo[1,2-a]pyridine-6-carboxylic acid and 1.2 g (3.9 mmol) O-(1H-benzotriazol-1-yl)-N,N,N',N'-tetramethyluronium tetrafluoroborate (TBTU) are suspended in 50 ml dichloromethane and 0.74 ml (6.0 mmol) methylamine (8 M in ethanol) are added to the reaction mixture. After stirring for 3 d at room temperature, the reaction mixture is hydrolyzed with saturated aqueous sodium hydrogencarbonate and extracted with ethyl acetate. The combined organic phases are dried over anhydrous magnesium sulphate and evaporated. Purification of the residue by column chromatography on silica gel using dichloromethane:methanol (20:1) and crystallization from diethyl ether/light petroleum ether yields 0.2 g (20%) of the title compound as a colourless solid (m.p. 143-144° C.).

6. 8-(trans-2,3-Dihydro-2-hydroxy-1-indenylamino)-2,3-dimethyl-imidazol-[1,2-a]pyridine-6-carboxamide 3.0 g (8.9 mmol) 8-(trans-2,3-dihydro-2-hydroxy-1-indenylamino)-2,3-dimethyl-imidazo[1,2-a]pyridine-6-carboxylic acid and 3.7 g (11.6 mmol) O-(1H-benzotriazol-1-yl)-N,N,N',N'-tetramethyluronium tetrafluoroborate (TBTU) are suspended in 150 ml dichloromethane and the mixture is stirred 1 h at room temperature. After ammonia gas is passed through the flask for 1.5 h, the reaction mixture is poured into 200 ml saturated aqueous ammonium chloride. The pH is adjusted to pH=7 by adding 6N hydrochloric acid and the mixture is extracted with dichloromethane. On evaporation of the organic phase, the product begins to crystallize and the precipitate is collected to yield 0.27 g (10%) of the title compound as a colourless solid (m.p. 162-163° C.).

7. Ethyl 8-hydroxy-2,3-dimethyl-imidazo[1,2-a]pyridine-6-carboxylate

A solution of 8.0 g (24.7 mmol) ethyl 8-benzyloxy-2,3-dimethyl-imidazo[1,2-a]pyridine-6-carboxylate in 80 ml ethanol is hydrogenated over 0.8 g 10% Pd/C (1 bar $H_2$) for 24 h. The catalyst is filtered off and the filtrate is evaporated. The oily residue is crystallized from diethyl ether to give 5.0 g (86%) of the title compound as a colourless solid (m.p. 219-221° C.).

8. 8-(trans-2,3-Dihydro-2-hydroxy-1-indenyloxy)-2,3-dimethyl-imidazo[1,2-a]pyridine-6-carboxylic acid To a suspension of 7.3 g (31.2 mmol) ethyl 8-hydroxy-2,3-dimethyl-imidazo[1,2-a]pyridine-6-carboxylate and 7.3 g (55.2 mmol) 1,2-epoxyindane in 150 ml methanol and 15 ml water are added 8.8 ml triethylamine and the reaction mixture is heated to 50° C. for 20 h. After cooling down, 100 ml ethyl acetate are added and the precipitate is collected by filtration. A second crop of material crystallizes from the mother liquor on evaporation. The total amount of precipitate is 6.0 g, which is suspended in a mixture of 100 ml dioxane and 60 ml 2N aqueous sodium hydroxide. After boiling under reflux for 1 h, the reaction mixture is evaporated to ⅓ of its volume and diluted with 15 ml methanol. The flask is placed in an ice bath and the pH is adjusted to pH=7 by adding 6N hydrochloric acid. After 30 min, the thick suspension is diluted with 20 ml methanol and filtered by suction. A second crop of material is obtained by evaporation of the mother liquor. The total amount of crude product is 6.75 g. Further purification is achieved by filtration over silica gel using dichloromethane:methanol:acetic acid (13:1:0.2) as eluent. Crystallization from methanol/diethyl ether yields 2.3 g (22%) of the title compound as a colourless solid (m.p. 229-231° C.).

9. 8-(trans-2,3-Dihydro-2-hydroxy-1-indenyloxy)-6-(N,N-dimethylamino-carbonyl)-2,3-dimethyl-imidazo[1,2-a]pyridine 2.0 g (5.7 mmol) 8-(trans-2,3-dihydro-2-hydroxy-1-indenyloxy)-2,3-dimethyl-imidazo[1,2-a]pyridine-6-carboxylic acid and 2.4 g (7.4 mmol) O-(1H-benzotriazol-1-yl)-N,N,N',N'-tetramethyluronium tetrafluoroborate (TBTU) are suspended in 100 ml dichloromethane and 2.1 ml (11.4 mmol) dimethylamine (5.6 M in ethanol) are added to the reaction mixture. After stirring for 3 h at room temperature, the reaction mixture is hydrolyzed with saturated aqueous sodium hydrogen carbonate. The organic phase is separated and the aqueous layer is extracted with dichloromethane The combined organic phases are dried over anhydrous magnesium sulphate and evaporated. Purification of the residue by column chromatography on silica gel using dichloromethane:methanol (20:1) and crystallization from methanol/light petroleum ether yields 1.18 g (57%) of the title compound as a colourless solid (m.p. 182-184° C.).

10. 8-Hydroxy-6-methoxymethyl-2,3-dimethyl-imidazo[1,2-a]pyridine

A solution of 3.0 g (10.1 mmol) 8-benzyloxy-6-methoxymethyl-2,3-dimethyl-imidazo[1,2-a]pyridine in 50 ml ethanol is hydrogenated over 0.3 g 10% Pd/C (1 bar $H_2$) for 1 h. The catalyst is filtered off and the filtrate is evaporated. The residue is crystallized from methanol/diethyl ether to give 1.2 g (57%) of the title compound as a colourless solid (m.p. 164-165° C.).

11. 8-(trans-2,3-Dihydro-2-hydroxy-1-indenyloxy)-6-methoxymethyl-2,3-dimethyl-imidazo[1,2-a]pyridine To a suspension of 1.0 g (4.9 mmol) 8-hydroxy-6-methoxymethyl-2,3-dimethyl-imidazo[1,2-a]pyridine and 1.3 g (9.7 mmol) 1,2-epoxyindane in 12 ml methanol and 3 ml water are added 1.4 ml triethylamine and the mixture is heated to 50° C. for 24 h. After cooling down, the reaction mixture is poured into 100 ml saturated aqueous ammonium chloride and extracted with dichloromethane. The organic phase is dried over anhydrous magnesium sulphate and evaporated. Purification of the residue by column chromatography on silica gel using dichloromethane:methanol (20:1) yields 0.7 g (45%) of the title compound as a colourless solid (m.p. 142-143° C.).

12. 8-Benzyloxy-6-(N,N-dimethylamino-carbonyl)-2,3-dimethyl-imidazo[1,2-a]pyridine To a solution of 51.5 g (155 mmol) 8-benzyloxy-6-bromo-1,2-dimethyl-imidazo[1,2-a]pyridine in 300 ml tetrahydrofuran and 50 ml triethylamine are added 5.15 g (23 mmol) palladium(II) acetate, 24 g (92 mmol) triphenylphosphine and 800 ml dimethylamine (2 M in tetrahydrofuran). The mixture is transferred to an autoclave and carbonylated (6-10 bar carbon monoxide pressure, 120° C.) for 16 h. The reaction mixture is cooled down, filtered and evaporated. The residue is dissolved in dichloromethane, extracted with water and evaporated. Purification of the residue by column chromatography on silica gel using dichloromethane:methanol (13:1) yields 41 g (81%) of the title compound as a colourless solid (m.p. 160° C.).

13. 6-(N,N-Dimethylaminocarbonyl)8-hydroxy-2,3-dimethyl-imidazo[1,2a]pyridine A mixture of 40 g (124 mmol) 8-benzyloxy-6-(N,N-dimethylaminocarbonyl)-2,3-dimethyl-imidazo[1,2-a]pyridine, 15 ml (154 mmol) 1,4-cyclohexadiene and 4 g 10% Pd/C in 400 ml ethanol is heated to reflux. After 3 h, the reaction mixture is cooled down, diluted with 400 ml dichloromethane and filtered. On evaporation, a precipitate is formed which is collected and dried in vacuo to give 24.5 g (85%) of the title compound as a colourless solid (m.p. 278-279° C.).

14. 8-[(1S,2S)-2,3-Dihydro-2-hydroxy-1-indenyloxy)-6-(N,N-dimethylamino-carbonyl)-2,3-dimethyl-imidazo[1,2-a]pyridine To a solution of 1.5 g (6.4 mmol) 6-(N,N-dimethylaminocarbonyl)-8-hydroxy-2,3-dimethyl-imidazo[1,2-a]pyridine in 30 ml ethanol and 7.5 ml water are added 1.7 g (12.9 mmol) (1R,2S)-epoxyindane and 1.8 ml triethylamine. After 3 h at 70° C., the mixture is cooled down and partitioned between dichloro-methane and water. The organic layer is separated, dried over anhydrous magnesium sulphate and evaporated. Purification of the residue by column chromatography on silica gel using ethyl acetate:light petroleum ether (1:1) and crystallization from diisopropyl ether yields 1.7 g (74%) of the title compound as a colourless solid (m.p. 122° C.).

15. 6-(N,N-Dimethylamino-carbonyl)-2,3-dimethyl-8-(trans-1,2,3,4-tetrahydro-2-hydroxy-1-naphthalenyloxy)-imidazo[1,2-a]pyridine hydrochloride To a solution of 1.0 g (4.3 mmol) 6-(N,N-dimethylamino-carbonyl)-8-hydroxy-2,3-dimethyl-imidazo[1,2-a]pyridine in 20 ml ethanol and 5 ml water are added 1.25 g (8.6 mmol) 1,2-epoxy-1,2,3,4-tetrahydro-naphthalene and 1.2 ml triethylamine. After 16 h at 80° C., the mixture is cooled down and partitioned between dichloromethane and saturated aqueous ammonium chloride. The organic layer is separated, dried over anhydrous magnesium sulphate and evaporated. Purification of the residue is achieved by column chromatography on silica gel using ethyl acetate:light petroleum ether (1:1), then dichloro-methane:methanol (20:1). The oil thus obtained is dissolved in ethyl acetate and treated with saturated hydrogen chloride in diethyl ether to give a precipitate which is collected and dried to yield 0.6 g (34%) of the title compound as a colourless solid (m.p. 129° C.).

16. 8-(trans-2,3-Dihydro-2-hydroxy-7-methoxy-1-indenyloxy)-6-(N,N-dimethylamino-carbonyl)-2,3-dimethyl-imidazo[1,2-a]pyridine To a solution of 0.8 g (3.4 mmol) 6-(N,N-dimethylamino-carbonyl)-8-hydroxy-2,3-dimethyl-imidazo[1,2-a]pyridine in 16 ml ethanol and 4 ml water are added 1.0 g (6.2 mmol) 1,2-epoxy-7-methoxy-indane and 0.48 ml triethylamine. After 4 h at 30° C., the mixture is cooled down and partitioned between di-chloromethane and saturated aqueous ammonium chloride. The organic layer is separated, dried over anhydrous magnesium sulphate and evaporated. Purification of the residue by column chromatography on silica gel using ethyl acetate:light petroleum ether:triethylamine (8:1:1) yields 0.26 g (19%) of the title compound as a colourless solid (m.p. 129° C.).

17. 8-(tans-2,3-Dihydro-2-hydroxy-7-methyl-1-indenyloxy)-6-(N,N-dimethylamino-carbonyl)-2,3-dimethyl-imidazo1,2-a]pyridine To a solution of 0.8 g (3.4 mmol) 6-(N,N-dimethylamino-carbonyl)-8-hydroxy-2,3-dimethyl-imidazo[1,2-a]pyridine in 16 ml ethanol and 4 ml water are added 0.9 g (1.2 mmol) 1,2-epoxy-7-methyl-indane and 0.48 ml triethylamine. After 5 h at 30° C., the mixture is cooled down and partitioned between ethyl acetate and saturated aqueous ammonium chloride. The organic layer is separated, dried over anhydrous magnesium sulphate and evaporated. Purification of the residue by column chromatography on silica gel using ethyl acetate:light petroleum ether:triethylamine (8:1:1) and crystallization from ethyl acetate/diethyl ether yields 0.26 g (20%) of the title compound as a colourless solid (m.p. 198° C.).

Commercial Utility

The compounds of the formula 1 and their salts have valuable pharmacological properties which make them commercially utilizable. In particular, they exhibit marked inhibition of gastric acid secretion and an excellent gastric and intestinal protective action in warm-blooded animals, in particular humans. In this connection, the compounds according to the invention are distinguished by a high selectivity of action, an advantageous duration of action, a particularly good enteral activity, the absence of significant side effects and a large therapeutic range.

"Gastric and intestinal protection" in this connection is understood as meaning the prevention and treatment of gastrointestinal diseases, in particular of gastrointestinal inflammatory diseases and lesions (such as, for example, gastric ulcer, duodenal ulcer, gastritis, hyperacidic or medicament-related functional dyspepsia), which can be caused, for example, by microorganisms (e.g. *Helicobacter pylori*), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula 1 and their pharmacologically acceptable salts are outstandingly suitable for use in human and veterinary medicine, where they are used, in particular, for the treatment and/or prophylaxis of disorders of the stomach and/or intestine.

A further subject of the invention are therefore the compounds according to the invention for use in the treatment and/or prophylaxis of the abovementioned diseases.

The invention likewise includes the use of the compounds according to the invention for the production of medicaments which are employed for the treatment and/or prophylaxis of the abovementioned diseases.

The invention furthermore includes the use of the compounds according to the invention for the treatment and/or prophylaxis of the abovementioned diseases.

A further subject of the invention are medicaments which comprise one or more compounds of the formula 1 and/or their pharmacologically acceptable salts.

The medicaments are prepared by processes which are known per se and familiar to the person skilled in the art. As medicaments, the pharmacologically active compounds according to the invention (=active compounds) are either employed as such, or preferably in combination with suitable pharmaceutical auxiliaries or excipients in the form of tablets, coated tablets, capsules, suppositories, patches (e.g. as TTS), emulsions, suspensions or solutions, the active compound content advantageously being between 0.1 and 95% and it being possible to obtain a pharmaceutical administration form exactly adapted to the active compound and/or to the desired onset and/or duration of action (e.g. a sustained-release form or an enteric form) by means of the appropriate selection of the auxiliaries and excipients.

The auxiliaries and excipients which are suitable for the desired pharmaceutical formulations are known to the person skilled in the art on the basis of his/her expert knowledge. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of several, preferably 1 to 4, individual doses to achieve the desired result. In the case of a parenteral treatment, similar or (in particular in the case of the intravenous administration of the active compounds), as a rule, lower doses can be used. The establishment of the optimal dose and manner of administration of the active compounds necessary in each case can easily be carried out by any person skilled in the art on the basis of his/her expert knowledge.

If the compounds according to the invention and/or their salts are to be used for the treatment of the abovementioned diseases, the pharmaceutical preparations can also contain one or more pharmacologically active constituents of other groups of medicaments, for example: tranquillizers (for example from the group of the benzodiazepines, for example diazepam), spasmolytics (for example, bietamiverine or camylofine), antcholinergics (for example, oxyphencyclimine or phencarbamide), local anesthetics, (for example, tetracaine or procaine), and, if appropriate, also enzymes, vitamins or amino acids.

To be emphasized in this connection is in particular the combination of the compounds according to the invention with pharmaceuticals which inhibit acid secretion, such as, for example, $H_2$ blockers (e.g. cimetidine, ranitidine), $H^+/K^+$ ATPase inhibitors (e.g. omeprazole, pantoprazole), or further with so-called peripheral anticholinergics (e.g. pirenzepine, telenzepine) and with gastrin antagonists with the aim of increasing the principal action in an additive or super-additive sense and/or of eliminating or of decreasing the side effects, or further the combination with antibacterially active substances (such as, for example, cephalosporins, tetracyclines, penicillins, macrolides, nitroimidazoles or alternatively bismuth salts) for the control of *Helicobacter pylori*. Suitable antibacterial co-components which may be mentioned are, for example, mezlocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (for example clarithromycin+metronidazole).

In view of their excellent gastric and intestinal protection action, the compounds of formula 1 are suited for a free or fixed combination with those medicaments (e.g. certain antiinflammatories and antirheumatics, such as NSAIDs), which are known to have a certain ulcerogenic potence. In addition, the compounds of formula 1 are particularly suited for a free or fixed combination with motility-modifying drugs.

Pharmacology

The excellent gastric protection and the gastric acid secretion-inhibiting action of the compounds according to the invention can be demonstrated in investigations on animal experimental models. The compounds according to the invention investigated in the model mentioned below have been provided with numbers which correspond to the numbers of these compounds in the examples.

Testing of the Secretion-Inhibiting Action on the Perfused Rat Stomach

In Table A which follows, the influence of the compounds according to the invention on the pentagastrin-stimulated acid secretion of the perfused rat stomach after intraduodenal administration in vivo is shown.

TABLE A

| No. | Dose (μmol/kg) i.d. | Inhibition of acid secretion (%) |
|---|---|---|
| 9 | 1 | >30 |
| 11 | 1 | >30 |
| 14 | 1 | >30 |
| 15 | 1 | >30 |
| 16 | 1 | >30 |
| 17 | 1 | >30 |

Methodology

The abdomen of anaesthetized rats (CD rat, female, 200-250 g; 1.5 g/kg i.m. urethane) was opened after tracheotomy by a median upper abdominal incision and a PVC catheter was fixed transorally in the oesophagus and another via the pylorus such that the ends of the tubes just projected into the gastric lumen. The catheter leading from the pylorus led outward into the right abdominal wall through a side opening.

After thorough rinsing (about 50-100 ml), warm (37° C.) physiological NaCl solution was continuously passed through the stomach (0.5 ml/min, ph 6.8-6.9; Braun-Unita I). The pH (pH meter 632, glass electrode EA 147; φ=5 mm, Metrohm) and, by titration with a freshly prepared 0.01N NaOH solution to ph 7 (Dosimat 665 Metrohm), the secreted HCl were determined in the effluent in each case collected at an interval of 15 minutes.

The gastric secretion was stimulated by continuous infusion of 1 μg/kg (=1.65 ml/h) of i.v. pentagastrin (left femoral vein) about 30 min after the end of the operation (i.e. after determination of 2 preliminary fractions). The substances to be tested were administered intraduodenally in a 2.5 ml/kg liquid volume 60 min after the start of the continuous pentagastrin infusion.

The body temperature of the animals was kept at a constant 37.8-38° C. by infrared irradiation and heat pads (automatic, stepless control by means of a rectal temperature sensor).

The invention claimed is:

1. A compound of the formula 1

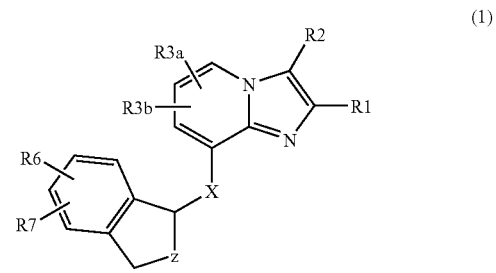

in which

R1 is hydrogen, 1-4C-alkyl, 3-7C-cycloalkyl, 3-7C-cycloalkyl-1-4C-alkyl, 1-4C-alkoxy, 1-4C-alkoxy- 1-4C-alkyl, 1-4C-alkoxycarbonyl, 2-4C-alkenyl, 2-4C-alkynyl, fluoro-1-4C-alkyl or hydroxy-1-4C-alkyl, R2 is hydrogen, 1-4C-alkyl, aryl, 3-7C-cycloalkyl, 3-7C-cycloalkyl-1-4C-alkyl, 1-4C-alkoxycarbonyl, hydroxy-1-4C-alkyl, halogen, 2-4C-alkenyl, 2-4C-alkynyl, fluoro-1-4C-alkyl, 1-4C-alkyl-aminomethyl or cyanomethyl, R3a is hydrogen, halogen, fluoro-1-4C-alkyl, 1-4C-alkyl, 2-4C-alkenyl, 2-4C-alkynyl, carboxyl, —CO-1-4C-alkoxy, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the group —CO—NR31R32, R3b is hydrogen, halogen, fluoro-1-4C-alkyl, 1-4C-alkyl, 2-4C-alkenyl, 2-4C-alkynyl, carboxyl, —CO- 1-4C-alkoxy, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the group —CO—NR31R32, where R31 is hydrogen, hydroxyl, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl,
or where
R31 and R32 together, including the nitrogen atom to which both are bonded, are a pyrrolidino, piperidino, piperazino, N-1-4C-alkylpiperazino or morpholino group, Z has the meaning —CHR4- or —CHR4-CHR5- where R4 is hydrogen, 1-7C-alkyl, 2-7C-alkenyl, hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino, R5 is hydrogen, 1-7C-alkyl, 2-7C-alkenyl, hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino, R6 is hydrogen, 1-4C-alkyl, hydroxy-1-4C-alkyl, 1-4C-alkoxy, 1-4C-alkoxy-1-4C-alkyl, 2-4C-alkenyloxy, 1-4C-alkylcarbonyl, carboxyl, 1-4C-alkoxycarbonyl, carboxy-1-4C-alkyl, 1-4C-alkoxycarbonyl-1-4C-alkyl, halogen, hydroxyl, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R7 is hydrogen, 1-4C-alkyl, 1-4C-alkoxy, 1-4C-alkoxycarbonyl, halogen, trifluoromethyl or hydroxyl, X is O (oxygen) or NH, and aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy, hydroxyl and cyano, or a salt thereof, with the provisos that (1) R3a is not hydrogen, halogen, 1-4C-alkoxy or —CO-1-4C-alkoxy when R3b is hydrogen, Z has the meaning —CHR4- and R4 is hydrogen or 1-7C-alkyl, (2) R3a is not hydrogen, halogen, 1-4C-alkoxy or —CO-1-4C-alkoxy when R3b is hydrogen, Z has the meaning —CHR4-CHR5-, R4 is hydrogen or 1-7C-alkyl and R5 is hydrogen or 1-7C-alkyl, (3) R3a is not hydrogen or halogen when R3b is hydrogen, Z has the meaning —CHR4- and R4 is hydroxyl, (4) R3a is not hydrogen or halogen when R3b is hydrogen, Z has the meaning —CHR4-CHR5-, one of R4 and R5 is hydroxyl and the other is hydrogen or 1-7C-alkyl, (5) R3a is not hydrogen when R3b is hydrogen, X is O (oxygen), Z has the meaning —CHR4- and R4 is 1-4C-alkoxy, 3-7C-cycloalkoxy, 1-4C-alkoxy-1-4C-alkoxy or 1-4C-alkylcarbonyloxy and (6) R3a is not hydrogen when R3b is hydrogen, X is O (oxygen), Z has the meaning —CHR4-CHR5-, one of R4 and R5 1-4C-alkoxy, 3-7C-cycloalkoxy, 1-4C-alkoxy-1-4C-alkoxy or 1-4C-alkylcarbonyloxy and the other is hydrogen.

2. A compound of the formula 1 according to claim 1, in which Z has the meaning —CHR4- and which is characterized by the formula 1-1

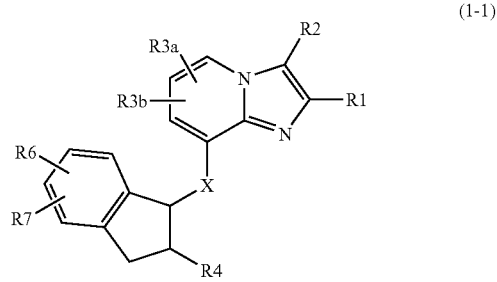

(1-1)

in which R1, R2, R3a, R3b, R4, R6, R7 and X have the meanings given in claim 1, or a salt thereof.

3. A compound of the formula 1 according to claim 1, in which Z has the meaning —CHR4-CHR5- and which is characterized by the formula 1-2

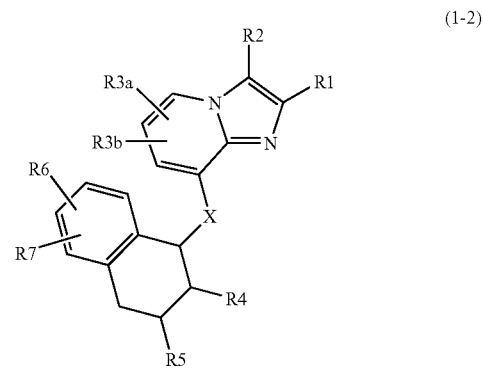

(1-2)

in which R1, R2, R3a, R3b, R4, R5, R6, R7 and X have the meanings given in claim 1, or a salt thereof.

4. A compound of formula 1 according to claim 1,
in which
R1 is 1-4C-alkyl,
R2 is hydrogen, 1-4C-alkyl or halogen,
R3a is in the 6-position and denotes carboxyl, —CO-1-4C-alkoxy, hydroxy-1-4C-alkyl, 1-4C-alkoxy-1-4C-alkyl or the group —CO—NR31R32,
where
R31 is hydrogen, 1-7C-alkyl, hydroxy-1-4C-alkyl or 1-4C-alkoxy-1-4C-alkyl and
R32 is hydrogen, 1-7C-alkyl, hydroxy-1-4C-alkyl or 1-4C-alkoxy-1-4C-alkyl,
or where
R31 and R32 together, including the nitrogen atom to which both are bonded, are a pyrrolidino, piperidino, piperazino, N-1-4C-alkylpiperazino or morpholino group,
R3b is hydrogen,
Z has the meaning —CHR4- or —CHR4-CHR5- where
R4 is hydroxyl,
R5 is hydrogen, R6 is hydrogen, 1-4C-alkyl or 1-4C-alkoxy,
R7 is hydrogen,
X is O (oxygen) or NH,
or a salt thereof.

5. A compound of formula 1-1 according to claim 2, in which
R1 is 1-4C-alkyl,
R2 is hydrogen, 1-4C-alkyl or halogen,
R3a is in the 6-position and denotes carboxyl, —CO-1-4C-alkoxy, hydroxy-1-4C-alkyl, 1-4C-alkoxy-1-4C-alkyl or the group —CO—NR31R32,
where
R31 is hydrogen, 1-7C-alkyl, hydroxy-1-4C-alkyl or 1-4C-alkoxy-1-4C-alkyl and
R32 is hydrogen, 1-7C-alkyl, hydroxy-1-4C-alkyl or 1-4C-alkoxy-1-4C-alkyl,
or where
R31 and R32 together, including the nitrogen atom to which both are bonded, are a pyrrolidino, piperidino, piperazino, N-1-4C-alkylpiperazino or morpholino group,
R3b is hydrogen,
R4 is hydroxyl,
R6 is hydrogen, 1-4C-alkyl or 1-4C-alkoxy,
R7 is hydrogen,
X is O (oxygen) or NH,
or a salt thereof.

6. An optically pure compound of formula 1-1 according to claim 2, which is characterized by the formula 1-1*

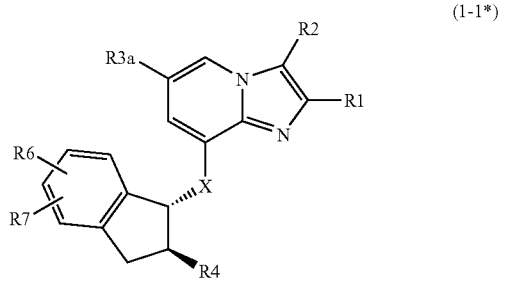

(1-1*)

and in which
R1 is 1-4C-alkyl,
R2 is hydrogen, 1-4C-alkyl or halogen,
R3a is in the 6-position and denotes carboxyl, —CO-1-4C-alkoxy, 1-4C-alkoxy-1-4C-alkyl, 1-4C-alkoxy-1-4C-alkoxy-1-4C-alkyl or the group —CO—NR31R32,
where
R31 is hydrogen, 1-7C-alkyl, hydroxy-1-4C-alkyl or 1-4C-alkoxy-1-4C-alkyl and
R32 is hydrogen, 1-7C-alkyl, hydroxy-1-4C-alkyl or 1-4C-alkoxy-1-4C-alkyl,
or where
R31 and R32 together, including the nitrogen atom to which both are bonded, are a pyrrolidino, piperidino, piperazino, N-1-4C-alkylpiperazino or morpholino group,
R4 is hydroxyl, 1-4C-alkoxy, oxo-substituted 1-4C-alkoxy, 3-7C-cycloalkoxy, 3-7C-cycloalkyl-1-4C-alkoxy, hydroxy-1-4C-alkoxy, 1-4C-alkoxy-1-4C-alkoxy, 1-4C-alkoxy-1-4C-alkoxy-1-4C-alkoxy, 3-7C-cycloalkoxy-1-4C-alkoxy, 3-7C-cycloalkyl-1-4C-alkoxy-1-4C-alkoxy, 1-4C-alkylcarbonyloxy, halo-1-4C-alkoxy, amino, mono- or di-1-4C-alkylamino, 1-4C-alkylcarbonylamino, 1-4C-alkoxycarbonylamino, mono- or di-1-4C-alkylamino-1-4C-alkylcarbonyloxy or 1-4C-alkoxy-1-4C-alkoxycarbonylamino,
R6 is hydrogen, 1-4C-alkyl, 1-4C-alkoxy or halogen,
R7 is hydrogen,
X is O (oxygen) or NH,
or a salt thereof.

7. A compound of formula 1-1* according to claim 6, in which
R1 is 1-4C-alkyl,
R2 is 1-4C-alkyl,
R3a is in the 6-position and denotes carboxyl, —CO-1-4C-alkoxy, 1-4C-alkoxy-1-4C-alkyl or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
R4 is hydroxyl,
R6 is hydrogen,
R7 is hydrogen,
X is O (oxygen) or NH,
or a salt thereof.

8. An optically pure compound of formula 1-2 according to claim 3, which is characterized by the formula 1-2*

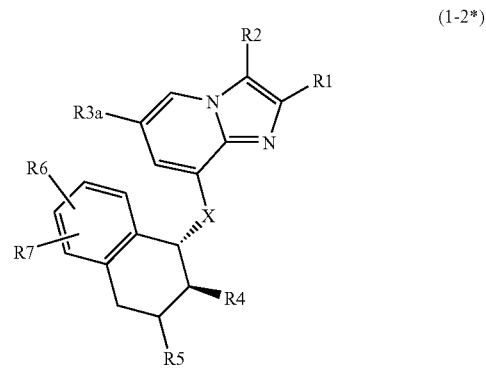

(1-2*)

in which
R1 is 1-4C-alkyl,
R2 is 1-4C-alkyl,
R3a is in the 6-position and denotes carboxyl, —CO-1-4C-alkoxy, 1-4C-alkoxy-1-4C-alkyl or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
R4 is hydroxyl,
R5 is hydrogen,
R6 is hydrogen,
R7 is hydrogen,
X is O (oxygen) or NH,
or a salt thereof.

9. A pharmaceutical composition comprising a therapeutically effective amount of a compound as claimed in claim 1 and/or a pharmaceutically acceptable salt thereof, together with a pharmaceutically acceptable auxiliary and/or excipient.

10. A method of treating a gastrointestinal disorder caused by gastric acid in a patient comprising administering to a patient in need thereof a compound of formula I as claimed in claim 1, or a pharmaceutically acceptable salt thereof.

11. A compound of the formula I, selected from the group consisting of

- Methyl 8-(trans-2,3-dihydro-2-hydroxy-1-indenylamino)-2,3-dimethyl-imidazo[1,2a]pyridine-6-carboxylate,
- 8-(trans-2,3-Dihydro-2-hydroxy-1-indenylamino)-2,3-dimethyl-imidazo[1,2-a]pyridine-6-carboxylic acid,
- 8-(trans2,3-Dihydro-2-hydroxy-1-indenylamino)-6-[N-(2-methoxyethyl)-amino-carbonyl]-2,3-dimethyl-imidazo[1,2-a]pyridine,
- 8-(trans-2,3-Dihydro-2-hydroxy-1-indenylamino)-6-(N,N-dimethylaminocarbonyl)-2,3-dimethyl-imidazo[1,2-a]pyridine,
- 8-(trans-2,3-Dihydro-2-hydroxy-1-indenylamino)-6-(N-methylamino-carbonyl)-2,3-dimethyl-imidazo[1,2-a]pyridine,
- 8-(trans2,3-Dihydro-2-hydroxy-1-indenylamino)-2,3-dimethy-imidazo[1,2-a]pyridine-6-carboxamide,
- 8-(trans-2,3-Dihydro-2-hydroxy-1-indenyloxy)-2,3-dimethyl-imidazo[1,2a]pyridine-6-carboxylic acid,
- 8-(trans-2,3-Dihydro-2-hydroxy-1-indenyloxy)-6-(N,N-dimethylamino-carbonyl)-2,3-dimethyl-imidazo[1,2-a]pyridine,
- 8-(trans-2,3-Dihydro-2-hydroxy-1-indenyloxy)-6-methoxymethyl-2,3-dimethyl-imidazo[1,2-a]pyridine,
- 8-[(1S,2S)-2,3-Dihydro-2-hydroxy-1-indenyloxy)-6-(N,N-dimethylamino-carbonyl)-2,3-dimethyl-imidazo[1,2-a]pyridine,
- 6-(N,N-Dimethylamino-carbonyl)-2,3-dirnethyl8-(trans-1,2,3,4-tetrahydro-2hydroxy-1naphthalenyloxy)-imidazo[1,2a]pyridine hydrochloride,
- 8-(trans-2,3-Dihydro-2hydroxy-7-methoxy-1-indenyloxy)-6-(N,N-dimethylamino-carbonyl)-2,3-dimethylimidazo[1,2-a]pyridine, and
- 8-(trans2,3-Dihydro-2-hydroxy-7-methyl-1-indenyloxy)-6-(N,N-dimethylaminocarbonyl)-2,3-dimethyl-imidazo[1,2-a]pyridine and salt thereof.

12. A method of treating a gastrointestinal disorder caused by gastric acid in a patient comprising administering to a patient in need thereof a compound of formula I as claimed in claim 1, or a pharmaceutically acceptable salt thereof, wherein the disorder is selected from the group consisting of gastric ulcer, duodenal ulcer, gastritis, hyperacidic related functional gastropathy, medicinally related functional gastropathy, reflux esophagitis, Zollinger-Ellison syndrome, heartburn and peptic ulcer bleeding.

\* \* \* \* \*

UNITED STATES PATENT AND TRADEMARK OFFICE
CERTIFICATE OF CORRECTION

PATENT NO.        : 7,326,718 B2
APPLICATION NO. : 10/534741
DATED             : February 5, 2008
INVENTOR(S)       : Buhr et al.

It is certified that error appears in the above-identified patent and that said Letters Patent is hereby corrected as shown below:

Claim 6, Column 23, Lines 30-44,
Please delete formula 1-1* and replace with correct formula 1-1* as shown

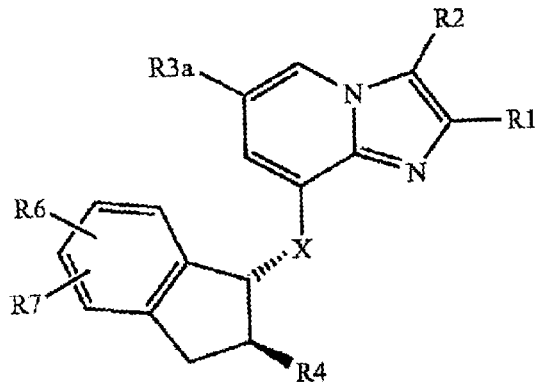

Claim 8, Column 24, Lines 27-43,
Please delete formula 1-2* and replace with correct formula 1-2* as shown

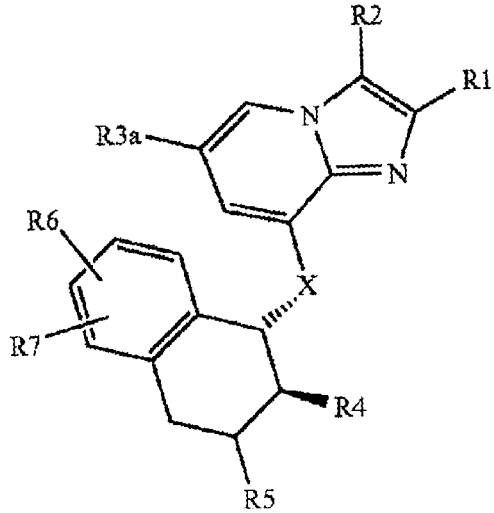

UNITED STATES PATENT AND TRADEMARK OFFICE
CERTIFICATE OF CORRECTION

PATENT NO. : 7,326,718 B2
APPLICATION NO. : 10/534741
DATED : February 5, 2008
INVENTOR(S) : Buhr et al.

It is certified that error appears in the above-identified patent and that said Letters Patent is hereby corrected as shown below:

Claim 11, Column 25, Lines 19-20,
Please delete "8-(trans2,3-Dihydro-2-hydroxy-1-indenylamino)-2,3-dimethy-imidazo[1,2-a]pyridine-6-carboxamide,"
and
replace with -- 8-(trans-2,3-Dihydro-2-hydroxy-1-indenylamino)-2,3-dimethyl-imidazo[1,2-a]pyridine-6-carboxamide, --

Claim 11, Column 26, Lines 6-8,
Please delete "6-(N,N-Dimethylamino-carbonyl)-2,3-dirnethyl8-(trans-1,2,3,4-tetrahydro-2hydroxy-lnaphthalenyloxy)-imidazo[1,2a]pyridine hydrochloride"
and
replace with -- 6-(N,N-Dimethylamino-carbonyl)-2,3-dimethyl-8-(trans-1,2,3,4-tetrahydro-2-hydroxy-1-naphthalenyloxy)-imidazo[1,2a]pyridine hydrochloride --

Claim 11, Column 26, Lines 9-11,
Please delete "8-(trans-2,3-Dihydro-2hydroxy-7-methoxy-1-indenyloxy)-6-(N,N-dimethylaminocarbonyl)-2,3-dimethylimidazo[1,2-a]pyridine, and"
and
replace with -- 8-(trans-2,3-Dihydro-2-hydroxy-7-methoxy-1-indenyloxy)-6-(N,N-dimethylaminocarbonyl)-2,3-dimethylimidazo[1,2-a]pyridine, and --

UNITED STATES PATENT AND TRADEMARK OFFICE
CERTIFICATE OF CORRECTION

PATENT NO. : 7,326,718 B2
APPLICATION NO. : 10/534741
DATED : February 5, 2008
INVENTOR(S) : Buhr et al.

It is certified that error appears in the above-identified patent and that said Letters Patent is hereby corrected as shown below:

Claim 11, Column 26, Lines 12-14,
Please delete "8-(trans2,3-Dihydro-2-hydroxy-7-methyl-l-indenyloxy)-6-(N,N-dimethylaminocarbonyl)-2,3-dimethyl-imidazo[1,2-a]pyridine and salt thereof."
and
replace with -- 8-(trans-2,3-Dihydro-2-hydroxy-7-methyl-l-indenyloxy)-6-(N,N-dimethylaminocarbonyl)-2,3-dimethyl-imidazo[1,2-a]pyridine and salts thereof. --

Signed and Sealed this

Fifteenth Day of July, 2008

JON W. DUDAS
*Director of the United States Patent and Trademark Office*